US012648814B2

(12) United States Patent
Petkov

(10) Patent No.: US 12,648,814 B2
(45) Date of Patent: Jun. 9, 2026

(54) TECHNIQUE FOR OPTICAL GUIDANCE DURING A SURGICAL PROCEDURE

(71) Applicant: SIEMENS HEALTHINEERS AG, Forchheim (DE)

(72) Inventor: Kaloian Petkov, Lawrenceville, NJ (US)

(73) Assignee: Siemens Healthineers AG, Forchheim (DE)

( * ) Notice: Subject to any disclaimer, the term of this patent is extended or adjusted under 35 U.S.C. 154(b) by 576 days.

(21) Appl. No.: 18/159,692

(22) Filed: Jan. 26, 2023

(65) Prior Publication Data

US 2023/0255692 A1    Aug. 17, 2023

(30) Foreign Application Priority Data

Feb. 16, 2022    (EP) ..................................... 22157029

(51) Int. Cl.
*A61B 34/10*        (2016.01)
*A61B 34/20*        (2016.01)
(52) U.S. Cl.
CPC ............... *A61B 34/10* (2016.02); *A61B 34/20* (2016.02); *A61B 2034/107* (2016.02)
(58) Field of Classification Search
CPC ......... A61B 34/10; A61B 34/20; A61B 34/25; A61B 90/36; A61B 2034/105; A61B 2034/107; A61B 2090/364; A61B 2090/365; A61B 2090/367; G06T 7/50; G06T 7/90; G06T 7/194; G06T 15/503; G06T 19/00; G06T 2207/10028; G06T 2207/30004; G06T 2210/41
See application file for complete search history.

(56) References Cited

U.S. PATENT DOCUMENTS 7,184,063 B2 *    2/2007    Shum ..................... G06T 11/001
                                                                345/640
10,565,774 B2    2/2020    Petkov
                           (Continued)

FOREIGN PATENT DOCUMENTS

CN        105979900 A      9/2016
CN        108882854 A      11/2018
                (Continued)

OTHER PUBLICATIONS

Alper S., Serkan D., Nathan N., Stefan Z., Aytek A., and Ingo W., Ray-traced Shell Traversal of Tetrahedral Meshes for Direct Volume Visualization, Nov. 30, 2021, IEEE, 2021 IEEE Visualization Conference (VIS), pp. 91-95 (Year: 2021).*

(Continued)

*Primary Examiner* — Jason Chan

(57)        ABSTRACT

Optical guidance is provided during a surgical procedure. Data indicative of an anatomical structure in relation to a surgical procedure is received. An overlay image of the anatomical structure is generated from the received data. A background structure serving as a background for the generated overlay image of the anatomical structure is determined. The generated overlay image of the anatomical structure is blended by a depth enhancement algorithm relative to the determined background structure. The blended image of the anatomical structure is overlaid on the determined background structure.

16 Claims, 8 Drawing Sheets

(56) References Cited

U.S. PATENT DOCUMENTS

| | | | | |
|---|---|---|---|---|
| 11,523,874 | B2 * | 12/2022 | Popovic | A61B 1/00194 |
| 11,771,520 | B2 | 10/2023 | Silva et al. | |
| 2019/0050665 | A1 * | 2/2019 | Sakuragi | A61B 6/022 |
| 2019/0094554 | A1 * | 3/2019 | Benesh | G06T 11/001 |
| 2019/0247130 | A1 | 8/2019 | State et al. | |
| 2021/0196385 | A1 * | 7/2021 | Shelton, IV | G16H 30/40 |
| 2021/0279942 | A1 | 9/2021 | Petkov et al. | |
| 2022/0175473 | A1 * | 6/2022 | Feather | G06T 15/40 |
| 2022/0343586 | A1 | 10/2022 | Vetter et al. | |
| 2023/0127380 | A1 * | 4/2023 | Ozer | G06T 7/11 |
| | | | | 382/128 |

FOREIGN PATENT DOCUMENTS

| | | | | |
|---|---|---|---|---|
| EP | 3553785 | A1 | 10/2019 | |
| EP | 3879498 | A1 | 9/2021 | |
| WO | 2015118423 | A1 | 8/2015 | |
| WO | WO-2020243425 | A1 * | 12/2020 | A61B 34/10 |

OTHER PUBLICATIONS

S. Bernhardt, S. A. Nicolau, L. Soler and C. Doignon, "The status of augmented reality in laparoscopic surgery as of 2016," Medical Image Analysis, 2017.

P. Vávra, J. Roman, P. Zonča, P. Ihnát, M. Němec, J. Kumar, N. Habib and A. El-Gendi, "Recent Development of Augmented Reality in Surgery: A Review," Journal of Helthcare Engineering, 2017.

L. Jud, J. Fotouhi, O. Andronic, A. Aichmair, G. Osgood, N. Navab and M. Farshad, "Applicability of augmented reality in orthopedic surgery—A systematic review," BMC Musculoskeletal Disorders, vol. 21, 2020.

C. Schneider, M. Allam, D. Stoyanov, D. Hawkes, K. Gurusamy and B. Davidson, "Performance of image guided navigation in laparoscopic liver surgery—A systematic review," Surgical Oncology, 2021.

C. Hansen, J. Wieferich, F. Ritter, C. Rieder and H.-O. Peitgen, "Illustrative visualization of 3D planning models for augmented reality in liver surgery," International Journal of Computer Assisted Radiology and Surgery, vol. 5, pp. 133-141, 2010.

E. Pelanis, A. Teatini, B. Eigl, A. Regensburger, A. Alzaga, R. P. Kumar, T. Rudolph, D. L. Aghayan, C. Riediger, N. Kvarnstrom, O. J. Elle and B. Edwin, "Evaluation of a novel navigation platform for laparoscopic liver surgery with organ deformation compensation using injected fiducials," Medical Image Analysis, vol. 69, 2020.

T. Kroes, "Exposure Render: An Interactive Photo-Realistic Volume Rendering Framework," PLOS ONE, vol. 8, No. 4, 2012.

A. Neubauer et al., "STEPS—an Application for Simuilation of Transsphernoidal Endonasal Pituitary Surgery," IEEE Visualization 2004, pp. 513-520.

IEEE Transactions on Visualization and Computer Graphics contribution by K. Petkov et al. "Interactive Visibility Retargeting in VR Using Conformal Visualization" (vol. 18, Issue 7, Jul. 2012).

European Search Report issued Jul. 26, 2022 in corresponding European Patent Application No. 22157029.4.

Hansen Christian et al:"illustrative visualization of 3d planning models for augmented reality in liver surgery", int j cars(2020)5:133-141, Jun. 19, 2009.

* cited by examiner

100

Receive Data — S102

Generate Overlay — S104

Determine Background — S106

Blend — S108

Overaly — S110

200

Interface — 202

Rendering Unit — 204

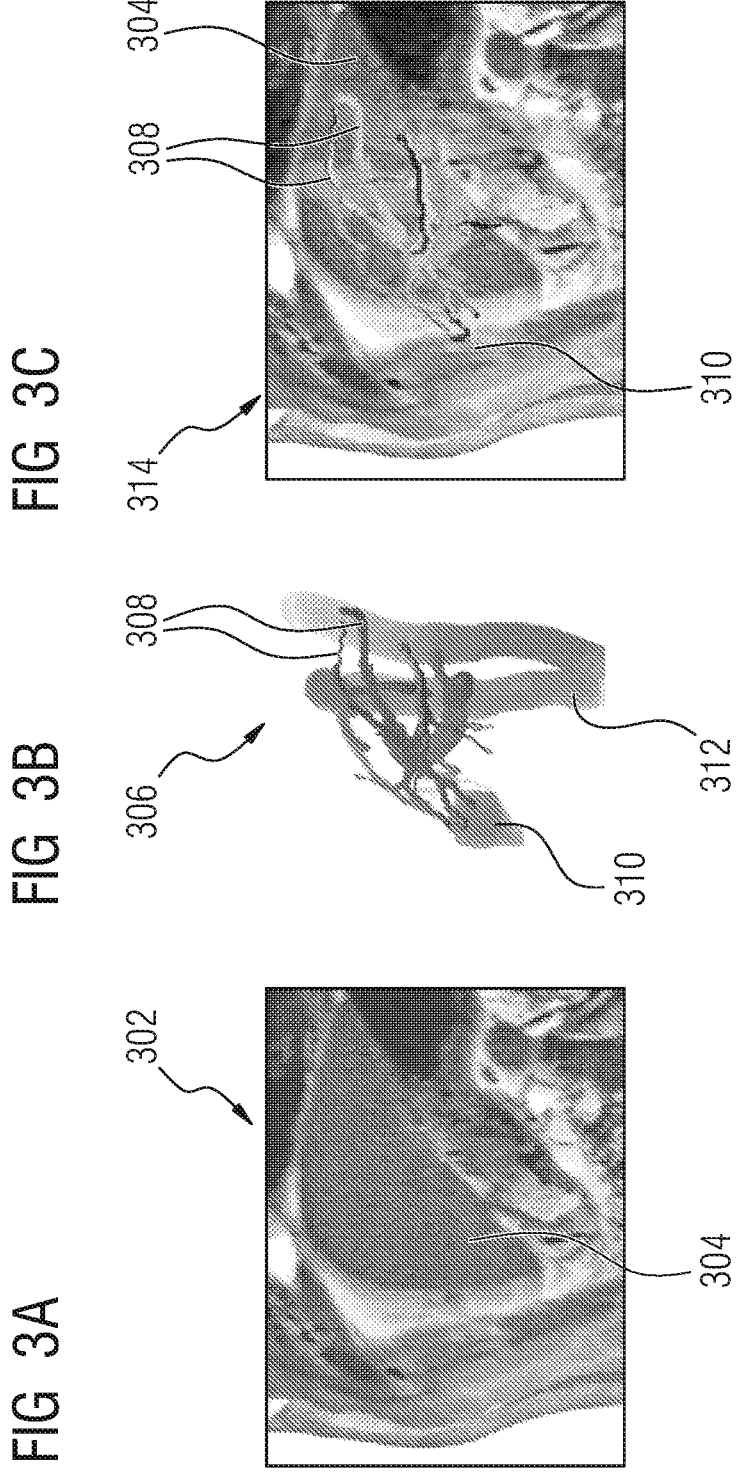

306

306-3    306-2    306-1

Depth-modulated opacity    Mesh Overlay    Depth Image 306-5    306-4

Depth-modulated opacity with volumetric tinting    Tinting computed with volume rendering

314

314-1    314-2

306-2

614

306-5

314

314-1

314-2

TECHNIQUE FOR OPTICAL GUIDANCE DURING A SURGICAL PROCEDURE

RELATED APPLICATION

This application claims the benefit of EP 22157029.4, filed Feb. 16, 2022, which is hereby incorporated by reference in its entirety.

TECHNICAL FIELD

The present document relates to an extended or augmented reality system for optical guidance during a surgical intervention.

BACKGROUND

Augmented reality (AR) for surgical support conventionally involves a display of three-dimensional (3D) data derived from pre-operative images over real-world images or videos. The accuracy and therefore the clinical utility of the data augmentation conventionally depend greatly on the type and quality of the patient image registration to the real world. The conventional techniques employed for 3D rendering further determine whether the AR image overlay conveys the correct depth information to the surgeon. Advanced techniques are typically required to reduce depth inconsistencies between the overlay and the real world.

Some of the conventional techniques for enhancing the depth perception of video overlays include plane clipping, distance fogging, and shape outlining, stereo disparity and motion parallax, occlusion from and shadowing of real-world surfaces, and wireframe rendering, as well as distance-encoding contours and surface lines. Tracking organ deformations using fiducial markers with simple overlay visualization of markers, resection margins and transparent resection models may be used.

The conventional techniques for procedure guidance rely on ad-hoc approaches addressing some individual aspects related to depth perception with limited use for optical guidance during surgical procedures.

SUMMARY AND DETAILED DESCRIPTION

It is therefore an object to provide a solution for improved optical guidance during a surgical procedure. Alternatively, or in addition, there is a need for a technique for improved and/or comprehensive depth perception in optically guided surgery. Further alternatively, or in addition, there is a need for a, in particular comprehensive, overlay implementation for photorealistic rendering for surgical guidance. Finally, quality of the guided interventional procedure should be improved.

This object is solved by a method for providing optical guidance during a surgical procedure (also denoted as medical intervention or interventional procedure, briefly: intervention), by a system (which may be embodied by a server, workstation and/or computer), by a computer program product and by a non-transitory computer-readable medium according to the appended independent claims. Advantageous aspects, features and embodiments are described in the dependent claims and in the following description together with advantages.

A method and a system provide optical guidance during a surgical procedure. Features, advantages, or alternative embodiments herein can be assigned to the other claimed objects (e.g., system, rendering unit or the computer program or a computer program product), and vice versa. In other words, claims for the system can be improved with features described or claimed in the context of the method. In this case, the functional features of the method are embodied by structural units of the system and vice versa, respectively.

According to a first aspect, a computer-implemented method (e.g., an application to be executed on a computer related to controlling optical guidance) provides optical guidance during a surgical procedure. The method includes a act of receiving data indicative of an anatomical structure in relation to a surgical procedure. The method further includes an act of generating an overlay image of the anatomical structure from the received data. The method further includes an act of determining a background structure serving as a background for the generated overlay image of the anatomical structure. The method further includes an act of blending the generated overlay image of the anatomical structure by means of a depth enhancement algorithm relative to the determined background structure. The method still further includes an act of overlaying the blended image of the anatomical structure on the determined background structure.

The surgical procedure may include an, e.g., minimal, invasive procedure. Alternatively, or in addition, the surgical procedure may include laparoscopic surgery (briefly: laparoscopy), thoracoscopic surgery, and/or endoscopic surgery. Further alternatively, or in addition, the surgical procedure may include open surgery.

The received data indicative of the anatomical structure may include data indicative of a lesion, blood vessels and/or bones. The planning of the surgical procedure (also briefly: surgery) may include tending to and/or treating the lesion, e.g., for excising the lesion during the surgical procedure. Alternatively, or in addition, the blood vessels may include blood vessels that should not be injured (and/or blood vessels that should be functionally preserved) during the surgical procedure, bones that need to be bypassed (and/or be functionally preserved) and/or blood vessels to be cut during the surgical procedure.

The received data indicative of the anatomical structure may be received pre-operatively (briefly: pre-op, also denoted as pre-surgically), e.g., from medical resonance imaging (MRI), a computed tomography (CT) scan, ultrasound, echocardiography and/or radiography. Alternatively, or in addition, the received data indicative of the anatomical structure may be received during the surgical procedure, e.g., from a camera attached to a surgical needle, from a gyroscopic sensor at a handle of a surgical device (also: surgical instrument), from ultrasound images, and/or from an external tracking system, e.g., optical tracking (which may also be denoted as reflective tracking) and/or from electromagnetic tracking. Further alternatively, or in addition, ultrasound, fluoroscopy and/or MRI may be used for intraoperative imaging of a, e.g., human, patient during the surgical procedure.

The surgical device may also be denoted as medical device. Alternatively, or in addition, the surgical device may include a tip and/or a needle.

The background structure may include a, e.g., live, image of an anatomical structure, including, surrounding and/or in the background of, an area on which the surgical procedure is planned to be performed. The, e.g., live, image may be obtained from a camera mounted on a surgical device, in particular a surgical needle.

Alternatively, or in addition, the, e.g., live image may include a part of a, in particular human, body on which open surgery is performed. Further alternatively, or in addition, the background structure may include a, e.g., live, image provided to a medical practitioner and/or a surgeon (also: user and/or, in particular human, observer, in particular in the context of rendering the overlayed image) during the surgical procedure.

The depth enhancement algorithm may include an algorithm that provides a realistic and/or appropriate image (or sequence of images) including the generated overlay image and the background structure. Alternatively, or in addition, the blended generated overlay image (shortly: the blended image) and the background image may include a (e.g., fused) image that fiducially depicts an anatomical area on which the surgical procedure is performed.

The (e.g., fused) image may be instantaneous and/or may change over time. Alternatively, or in addition, the method may include performing at least the acts of generating the overlay image, blending the generated overlay image and overlaying the blended image on the determined background for every instant in time and/or any image within a sequence of images (e.g., within a real-time video including the background structure). The sequence of images in time may also be denoted as (e.g., generalized) cinematographic image (or shortly: e.g., generalized, cine image), as live feed, and/or a real-time video (also: video feed).

Alternatively, or in addition, the method may include performing at least the acts of generating the overlay image, blending the generated overlay image and overlaying the blended image on the determined background for an asynchronous (e.g., blended) overlay image and determined background (e.g., the overlay image may be updated at a slower rate and/or less frequently than a real-time video including the background structure). Further alternatively, or in addition, the sequence of overlayed images may include components updated at different frequencies. E.g., the blended overlay image may be updated with a first frequency and the determined background (and/or the determined background structure) may be updated with a second frequency. The second frequency may be higher than the first frequency.

The act of overlaying the blended image on the determined background structure may include registering the blended image and the background structure. The registering (also denoted as the registration) may be between three-dimensional (3D) data used to render the (e.g., blended) overlay image (e.g., including at least part of an organ, one or more vessels and/or a lesion) and the three-dimensional (3D) anatomical structures detected in the background (e.g., in a background image and/or in the background structure).

Alternatively, or in addition, the act of overlaying the blended image on the determined background structure may include applying one or more fiducial markers for the positioning. E.g., fiducial markers may be used for tracking a surgical device (e.g., a surgical needle), in particular in a laparoscopic video feed. Alternatively, or in addition, the positioning may include a two-dimensional image plane. Further alternatively, or in addition, the positioning may include a three-dimensional orientation of the blended image relative to a projection of the background structure (e.g., onto the two-dimensional image plane).

Anatomical structures and medical devices may be detected from intraoperative imaging. E.g., for reconstructing vessel trees, the position and orientation of a transesophageal echocardiography (TEE) probe may be detected from one or more live fluoroscopic images. TEE may include high-frequency sound waves (ultrasound) produced by an echo transducer attached to a thin tube which is passed through the mouth and throat into the esophagus of the patient. The fluoroscopic image(s) may be augmented with the TEE images (e.g., using Syngo TrueFusion by Siemens). By the augmentation, one or more overlayed images of the blended image onto the background structure may be produced.

Alternatively, or in addition, a manual (e.g., by the user and/or a surgeon) or semi-automated calibration may be performed, e.g., for determining a relative positioning when overlaying the blended image onto the background structure.

By the method, coherent (e.g., photorealistic) rendering of a surgical environment is enabled. Coherent rendering may include providing a reliable and/or trustworthy guidance for a medical practitioner and/or surgeon during the surgical procedure. The coherent rendering may include non-photorealistic graphics. Alternatively, or in addition, at least part of the rendering, e.g., including the background structure, may be photorealistic.

According to a preferred embodiment, the blending (e.g., of the overlay image) includes a color tinting (also denoted as volume tinting), optionally depending on the determined background structure.

So-called alpha blending may be used on both the overlay image and the background structure.

Alternatively, or in addition, distance-based (e.g., color) tinting of the overlay image may modify the color of the overlay image. By tinting (e.g., only) the color of the overlay image, a (e.g., correct) depth perception may be induced when overlaying the overlay image onto the background structure (also denoted as base image).

The color tinting may include, or may correspond to, an implicit depth perception.

Alternatively, or in addition, depth information may be provided by color tinting. Further alternatively, or in addition, the depth perception may be improved compared to conventional rendering techniques based on color tinting (e.g., including a volumetric fog).

Fog-like depth (e.g., color) tinting may be an explicit effect, e.g., on the overlay image. By implementing a photorealistic overlay based on the overlay image, to which (e.g., fog-like depth) tinting is applied, the effect is implicit on the overlay including both the overlay image and the background structure.

A color may be lighter and/or more intense for parts of the anatomical structure nearer to an observer than a color of parts of the anatomical structure farther from the observer (e.g., the surgeon).

Alternatively, or in addition, the blending may include selecting and/or applying an opacity of the overlay image of the anatomical structure depending on the depth enhancement algorithm.

The opacity may be increased for parts of the anatomical structure nearer to the observer, and the opacity may be diminished for parts of the anatomical structure farther from the observer (e.g., the surgeon).

Alternatively, or in addition, a transparency may be diminished for parts of the anatomical structure nearer to the observer, and the transparency may be increased for parts of the anatomical structure farther from the observer (e.g., the surgeon).

Transparency may be the inverse of opacity, e.g., a value of the transparency may be one minus the value of the opacity.

Alternatively, or in addition, the blending may include a combination of the color tinting and selection of the opacity, in particular depending on the determined background structure.

According to another preferred embodiment, the color tinting includes a coloring relative to a predetermined value depending on the determined background structure.

The predetermined value may depend on a classification of the background structure. E.g., the background structure may be classified in terms of organs of the, in particular human, body. A coloring of the background structure may include predetermined colors according to the organs. Organs may, e.g., include the liver, kidneys, intestine, and/or gall bladder for laparoscopic surgery, and/or the lung, heart and/or pleura for thoracoscopic surgery.

Alternatively, or in addition, the color tinting may include a coloring determined (e.g., computed) for a three-dimensional (3D) volume rendering of (e.g., full) pre-surgical (also denoted as pre-operational, briefly: pre-op) imaging data, in particular using a photorealistic renderer.

Further alternatively, or in addition, the color tinting may (e.g., partially and/or as a starting point subject to subsequent adjustments and/or changes) include a fixed coloring, e.g., according to a distance fog.

According to another preferred embodiment, the blending includes a depth modulated opacity.

By performing color tinting and/or depth modulated opacity, the depth perception of the (e.g., fused) image may be improved, in particular when both color tinting and depth modulated opacity are combined.

According to another preferred embodiment, the background structure includes image data acquired in a pre-operative scan. Alternatively, or in addition, according to another preferred embodiment, the background structure includes live image data acquired during the surgical procedure.

The image data acquired in the pre-operative scan may include MRI, a CT scan, ultrasound, echocardiography and/or radiographs.

The live image data (also denoted as intraoperative image data) may be ultrasound data, echocardiography data, fluoroscopic image data, MRI data and/or camera data, e.g., located at a needle, acquired during the surgical procedure.

Alternatively, or in addition, image data acquired pre-operatively may be combined with live image data.

According to another preferred embodiment, the surgical procedure includes an open surgery, and the background structure includes a part of a, in particular human, body on which the surgical procedure is performed. According to this embodiment, the blended overlay image is, e.g., directly, projected onto the background structure. Alternatively, or in addition, according to this embodiment, the background structure, onto which the blended image is overlayed, may dispense with a live video feed.

According to another preferred embodiment, the blending includes a fading of the generated overlay image according to a depth relative to the determined background structure, wherein a degree of fading corresponds to the depth within the determined background structure. The degree of fading may be determined by the depth enhancement algorithm.

According to another preferred embodiment, a depth perception is obtained by means of a signed distance field (SDF), Monte Carlo path tracing and/or a ray tracing acceleration structure, in particular including a bounding volume hierarchy (BVH) and/or a K-dimensional tree (briefly: K-d tree).

The signed distance field (SDF) may also be denoted as signed distance function, or shortly as distance field. Alternatively, or in addition, the SDF includes a position as an input and outputs a distance from the position to a nearest part of a shape (e.g., segmented organ and/or vessel and/or medical device and/or body or part thereof). Further alternatively, or in addition, the SDF includes a subtraction of an inverted Euclidean distance transform (EDT) from an original EDT. Still further alternatively, or in addition, a negative value of the output of the SDF may correspond to a position inside a contour of the shape and a positive value of the output of the SDF corresponds to a position outside the contour of the shape, or vice versa. The contour and/or the shape may include a vessel wall and/or a (e.g., inner and/or outer) surface of an organ (e.g., liver and/or kidney).

(E.g., physically-based) Monte Carlo path tracing and/or ray tracing (also briefly path tracing and/or ray tracing) may be used to simulates light path though volume data with multiple scattering events per path using a stochastic process. As more and more paths and/or rays are simulated, the solution converges on an accurate estimation of the irradiance at each point for incoming light from all directions. A renderer may employ a hybrid of volumetric scattering and surface-like scattering, modeled by phase functions and bidirectional reflectance distribution functions (BRDFs), respectively, based on properties derived from anatomical data, in particular the anatomical structures of the overlay image and/or the corresponding background structure.

The BVH may include a tree-structure on a set of geometric objects (e.g., including circles, ellipses, triangles, rectangles and/or any further polygon), e.g., all of them wrapped in bounding volumes that form the leaf nodes of the tree. The nodes may be grouped as small sets and enclosed within larger bounding volumes, which in turn may be grouped and enclosed within other larger bounding volumes in a recursive fashion. By the BVH, ray tracing and/or collision detection may be efficiently performed.

The K-d tree (also denoted as special case of a binary space partition tree) is a binary tree in which every node is a k-dimensional point. It may include a space-partitioning data structure for organizing points in a K-dimensional space.

BVH data structures and/or K-d tree data structures may be used to accelerate spatial queries, e.g., how close a point is to a surface structure, and/or tray-surface intersections, e.g., a distance to a liver surface along the movement path of a surgical device such as a needle.

In some embodiments, both BVH and K-d tree may be used interchangeably. Alternatively, or in addition, a spatial subdivision may be applied, e.g., simpler octrees.

The SDF, ray tracing structure, BVH and K-dimensional tree are examples of data structures used for rendering the (e.g., blended) overlay image based on e.g., pre-surgical and/or pre-operative, three-dimensional (3D) data and/or on real-time (also denoted as live) three-dimensional (3D) data. The rendering of the (e.g., blended) overlay image may match the images and/or a video feed of the background structure during the surgical procedure.

The depth perception may be obtained as a result of a rendering algorithm that uses one or more of the above data structures, or any further suitable data structure. The rendering algorithm may include the depth enhancement algorithm.

For example, by the SDF, the BVH and/or the K-d tree, the pre-operatively generated overlay image may be adjusted and/or changed according to a movement of the line of sight, and/or a change of perspective, of the background structure.

According to another preferred embodiment, overlaying the blended image includes rendering the overlayed blended image using a video stream on a display.

The video stream may in particular be used for, e.g., minimal, invasive surgery. Alternatively, or in addition, the video stream may be used if the region of interest (ROI) cannot be brought into a line of sight of a human observer (e.g., a surgeon). E.g., the line of sight might be restricted by a, in particular fixed, positioning of a patient during the surgical procedure.

The display may include one or more monitors in an operating theatre (also: operating room), in which the surgical procedure is performed. Alternatively, or in addition, the display may include an augmented reality (AR) headset. The AR headset may be used by the medical practitioner and/or the surgeon during the surgical procedure.

According to another preferred embodiment, generating the overlay image of the anatomical structure includes generating the overlay image by means of primitives.

The primitives may include one or more types of simple geometric objects, in particular points, lines or meshes.

According to another preferred embodiment, the blending includes generating a glyph indicative of an extent and/or a depth of at least part of the anatomical structure. The glyph may include a number of superimposed contours. Optionally, an intensity of the blending is varied so that the intensity is increased for the contour nearest to the observer and the intensity is diminished for the contour farthest from the observer. Alternatively, or in addition, a line thickness, and/or a length and/or distance of dashes and/or dots, of the contour nearest to the observer is increased and the line thickness, and/or length and/or distance of dashes and/or dots, of the contour is decreased for the contour farthest from the observer.

Alternatively, or in addition, the glyph may include a distance line and/or extruded contour (which may also be denoted as a stilt and/or a picket). A tip of the distance line and/or of the extruded contour may denote a position of the at least part of the anatomical structure.

According to an embodiment, an outline of an object may be determined (e.g., computed) along a direction. E.g., a lesion outline may include an extrusion and/or multiple contours (also: extruded contours) along the direction to the closest point on the surface of an organ (e.g., the liver). The direction may alternatively be to the tip of the surgical device (e.g., needle) during the surgical procedure (e.g., laparoscopy).

Further alternatively, or in addition, the glyph may include a numerical depth indication.

According to an embodiment, the contours may be at fixed pre-determined distance (e.g., relative to neighboring contours). By the fixed pre-determined distance, markings on a ruler may be mimicked for quick visual estimation of distances.

According to a further embodiment, an adaptation of the contour density may reduce clutter, e.g., tightly spaced contours near critical regions (e.g., including a lesion), and/or a different visualization style, e.g., a thinner and/or more transparent line (e.g., corresponding to the depth indication and/or near the critical regions).

Each of the number of superimposed contours may be, e.g., up to an overall scaling, identical in shape. The deeper the contour, the smaller the scaling may be chosen, e.g., according to a three-dimensional foreshortening and/or a three-dimensional camera perspective. According to an alternative embodiment, the superimposed contours may, e.g., all, have the same size.

Alternatively, or in addition, the deeper the contour the more transparent (and/or the less opaque) and/or the more color tinted (e.g., the darker) the contour may be. Further alternatively, or in addition, the deeper the contour, the thinner the line thickness may be, or the shorter the length of dashes of a dashed line, or the smaller the distances between neighboring dashes and/or dots of a dashed, dotted or dash-dotted line may be. Further alternatively, or in addition, the changes in transparency (and/or opacity), color tinting, line thickness, dashes and/or dots may be combined in dependence of the depth of the contour.

The contour farthest from the observer may correspond to the position of the anatomical structure within the background structure.

The distance line and/or extruded contour (and/or the stilt and/or the picket) may have the shape of a needle pointing towards the at least part of the anatomical structure.

The numerical depth indication may include a length, e.g., measured in millimeters (mm). The numerical depth indication may be rendered jointly with, and/or in the vicinity of, one of the superimposed contours, the distance line, and/or the extruded contour.

According to another preferred embodiment, the overlaying includes prioritizing a surgical device over the blended image. Prioritizing the surgical device may include the surgical device occluding (e.g., completely and/or without any blending effects such as color tinting and/or depth modulated opacity) the anatomical structure if the depth of anatomical structure lies below the surgical device. "Lying below the surgical device" may refer to a perspective from an observer, e.g., a medical practitioner (and/or surgeon) performing the surgical procedure.

According to a second aspect, a system provides optical guidance during a surgical procedure. The system includes an interface configured to receive data indicative of an anatomical structure in relation to a surgical procedure. The system further includes a rendering unit (renderer or graphics processing unit) configured to generate an overlay image of the anatomical structure from the received data. The rendering unit is further configured to determine a background structure serving as a background for the generated overlay image of the anatomical structure. The rendering unit is further configured to blend the generated overlay image of the anatomical structure by a depth enhancement algorithm relative to the determined background structure. The rendering unit is still further configured to overlay the blended image of the anatomical structure on the determined background structure.

In still another aspect, the rendering unit (renderer) is equipped with the interface configured to receive data indicative of an anatomical structure in relation to a surgical procedure.

The rendering unit may be embodied by, or may include, a graphics processing unit (GPU). Alternatively, or in addition, the system may be embodied by, or may include, a server and/or a computer, in particular a workstation, including a GPU.

According to a further aspect, a computer program product includes program elements (instructions), which induce a server to carry out the acts of the method for providing optical guidance during a surgical procedure according to the method of the first aspect, when the program elements are loaded into a memory of the server.

According to a still further aspect, a non-transitory computer-readable medium stores program elements (instructions) that can be read and executed by a server, in order to perform acts of the method for providing optical guidance during a surgical procedure according to the first aspect, when the program elements are executed by the server. The computer program product may also be provided for download, e.g., via a radio or cellular network, the Internet and/or a host computer. Alternatively, or in addition, the method may be encoded in a Field-Programmable Gate Array (FPGA) and/or an Application-Specific Integrated Circuit (ASIC), or the functionality may be provided for download by a hardware description language.

The properties, features and advantages described above, as well as the manner they are achieved, become clearer and more understandable in the light of the following description and embodiments, which will be described in more detail in the context of the drawings. This following description does not limit the invention on the contained embodiments. Same components or parts can be labeled with the same reference signs in different figures. In general, the figures are not for scale.

It shall be understood that a preferred embodiment of the present invention can also be any combination of the dependent claims or above embodiments with the respective independent claim.

These and other aspects of the invention will be apparent from and elucidated with reference to the embodiments described hereinafter.

BRIEF DESCRIPTION OF THE DRAWINGS

FIGS. 3A, 3B and 3C show a first example of a background structure, an overlay image and an overlay of the blended overlay image onto the background structure, respectively;

Any reference signs in the claims should not be construed as limiting the scope.

DETAILED DESCRIPTION OF THE PREFERRED EMBODIMENTS

Figures 1, 2:
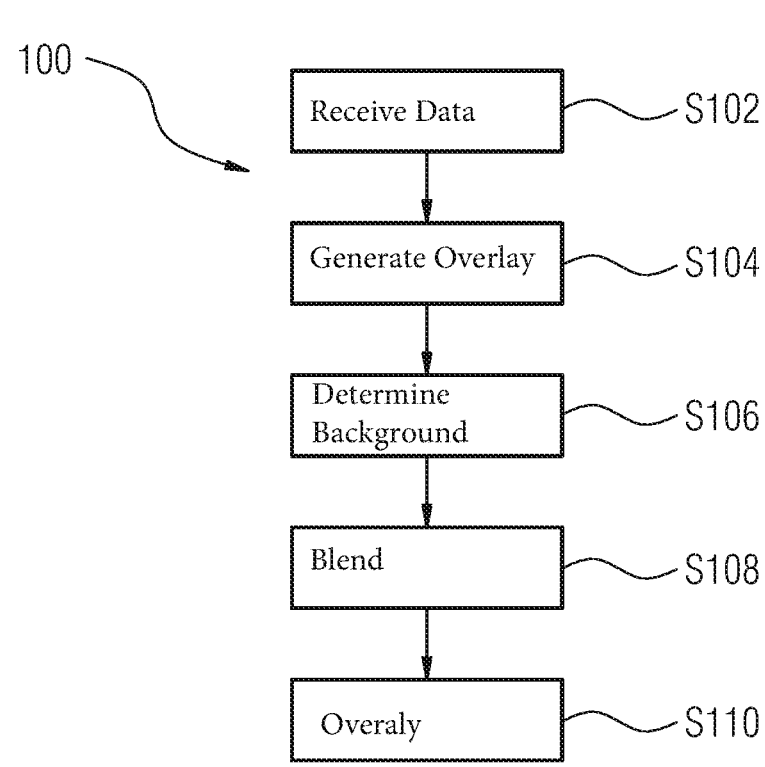
FIG. 1 is a flow chart of a method according to a preferred embodiment.
FIG. 2 is an overview of a system according to a preferred embodiment.

FIG. 1 shows an exemplary flowchart of a computer-implemented method for providing optical guidance during a surgical procedure. The method is generally referred to by reference sign 100.

The method 100 includes an act S102 of receiving data indicative of an anatomical structure in relation to a surgical procedure. The method 100 further includes an act S104 of generating an overlay image of the anatomical structure from the received S102 data. The method 100 further includes an act S106 of determining a background structure serving as a background for the generated S104 overlay image of the anatomical structure. The method 100 further includes an act S108 of blending the generated S104 overlay image of the anatomical structure by a depth enhancement algorithm relative to the determined S106 background structure. The method 100 still further includes an act S110 of overlaying the blended S108 image of the anatomical structure on the determined S106 background structure.

FIG. 2 shows an exemplary system for providing optical guidance during a surgical procedure. The system is generally referred to by reference sign 200.

The system 200 includes an interface 202 configured to receive data indicative of an anatomical structure in relation to a surgical procedure. The system 200 further includes a rendering unit 204 (renderer) configured to generate an overlay image of the anatomical structure from the received data. The rendering unit 204 is further configured to determine a background structure serving as a background for the generated overlay image of the anatomical structure. The rendering unit 204 is further configured to blend the generated overlay image of the anatomical structure by means of a depth enhancement algorithm relative to the determined background structure. The rendering unit 204 is still further configured to overlay the blended image of the anatomical structure on the determined background structure.

Alternatively, or in addition, the system 200 may be configured to perform the acts of the method 100. E.g., the interface 202 may be configured to perform the act S102. Alternatively, or in addition, the rendering unit 204 may be configured to perform at least one of the acts S104, S106, S108 and S110.

The system 200 may be embodied by a computer, in particular a server and/or a workstation. Alternatively, or in addition, the rendering unit 204 may be embodied by a GPU.

By the method 100 and/or the system 200, an augmented reality (AR) surgery support with model-based depth enhancement may be provided.

The method 100 and/or the system 200 tackle the challenge of providing surgeons with an accurate perception of depth (also: depth perception) when using image guidance with an AR overlay during a surgical procedure (e.g., in real-time). By the accurate depth perception, a safety and/or focus of a surgical procedure can be improved. E.g., lesions to surrounding textures due to the surgery can be avoided and/or a minimal invasive treatment on a precisely defined location can be performed.

One typical surgical procedure (also denoted as surgery and/or application) is in laparoscopy, where vessel and lesion segmentation from pre-operative images and resection planning data may be useful when displayed together with the live feed from the laparoscopic camera.

Further typical (in particular minimal invasive) surgical procedures include brain surgery and heart surgery. The method 100 and/or system 200 may be used for any further kind of surgical procedure, e.g., thoracoscopy, endoscopic surgery and/or any kind of surgery on joints, e.g., a knee and/or elbow.

Having reliable and easy to understand spatial perception, particularly including depth perception, of interior tissues and structures from the image guidance is paramount to realizing patient outcome improvements. A holistic augmentation method and system is provided.

The depth perception of the planning and segmentation data may be improved through one or more of the following features. The overlay may be photorealistic for rendering an enhanced depth perception. The photorealistic overlay may include, e.g., shadows, ambient light occlusions, depth of field, accurate matching of physical camera and real-world lighting. Alternatively, or in addition, a model-based volumetric coloring (also denoted as color tinting) may be applied. Overlay structures may be embedded, e.g., in registered pre-operative patient data and/or in reference anatomical models for more accurate color, occlusions and distance-based effects. Further alternatively, or in addition, an explicit rendering of distances via three-dimensional (3D) glyphs may be provided that visually "anchor" the overlay three-dimensional (3D) structures (also denoted as the blended overlay images of anatomical structure) to the real-world images (also denoted as the background structure).

FIGS. 3A, 3B and 3C show a first exemplary generation of an overlay for AR surgery support with opacity modulation and model-based volumetric tinting (also denoted as color tinting) for enhanced depth perception.

FIG. 3A shows an example of a background structure 302. In this example, the background structure 302 includes the liver 304 of a patient. Alternative examples in the context of laparoscopy may include the removal of the gall bladder, removal of the appendix, surgery for inguinal hernia, colon resection, stomach stapling operation, gastric stapling (or deactivating the small intestine), and sterilization (or fallopian tube sectioning).

Further examples for surgical procedure include heart surgery and brain surgery with corresponding background structures 302.

FIG. 3B shows an example of an overlay image 306. In this example, the overlay image 306 includes a lesion (e.g., benign, cancerous and/or tumor) 310 and various main blood vessels. E.g., the main blood vessels may include the aorta, the inferior vena cava (IVC), depicted with reference numeral 312, the hepatic artery (HA), the portal vein (PV), depicted with reference numeral 308 and the hepatic vein (HV). For example, at reference sign 312, the IVC may be depicted and at reference sign 308, the PV may be depicted. The example of FIG. 3B may be obtained from CT.

FIG. 3C shows an example of an overlay 314 of a blended version of the overlay image 306 onto the background structure 302 of FIGS. 3B and 3A, respectively. For example, the overlay image 306 may be blended and composited on top of real-world images as the background structure 302, e.g., as the video feed of a laparoscopic camera.

The overlay 314 may, e.g., be displayed on a screen in an operating theater (also denoted as operating room and/or surgical room). Alternatively, or in addition, the overlay image 306 may be displayed on an AR headset. By the display on the AR headset, the user and/or the surgeon may experience a virtual overlay analogous to the overlay 314.

The technique replaces some of the conventional ad-hoc approaches with real-time, e.g., photorealistic, rendering of segmented anatomical structures. The anatomical structures are further embedded in registered volumetric reference models or patient pre-operative three-dimensional (3D) image data (e.g., as the background structure 302) to compute more accurately (in particular compared to conventional techniques) occlusions, opacity modulation and color tinting compared to the existing approaches (e.g., compared to a fixed fog effect). Compared to many conventional systems, which rely on rasterization for performance reasons, the use of real-time raytracing and/or path tracing as taught herein also allows for accurate simulations of complex camera, lens and/or lighting parameters, which further increases the AR overlay precision.

The model-based volumetric tinting (also: color tinting) may be determined (e.g., computed) by having segmentation surfaces embedded in a transparent volumetric representation of an organ (e.g., the liver). The background structure 302 may be a cross-sectional rendering of the organ (e.g., the liver) as a solid tissue. Alternatively, or in addition, it may be (e.g., only) used for blending as a stand-in for base images and/or video frames acquired during the surgical procedure. Further alternatively, or in addition, the rendering of the background structure 302 may include a static volumetric fog.

Conventional volume visualization methods based on ray casting, which are still used in many current advanced visualization medical products, simulate only the emission and absorption of radiant energy along the primary viewing rays through the volume data. The emitted radiant energy at each point is absorbed, e.g., according to the Beer-Lambert law, along the ray to the observer location with absorption coefficients derived from the patient data. Renderers typically compute shading using only the standard local shading models at each point along the ray (e.g., the Blinn-Phong model), based on the local volume gradients (also denoted as local illumination). While fast, the conventional methods do not simulate the complex light scattering and extinction associated with photorealism (also denoted as global illumination).

Physically-based Monte Carlo light transport simulates light paths and/or rays though the volume data with multiple scattering events per path using a stochastic process. As more and more paths and/or rays are simulated, the solution converges on an accurate estimation of the irradiance at each point for incoming light from all directions. The renderer employs a hybrid of volumetric scattering and surface-like scattering, modeled by phase functions and bidirectional reflectance distribution functions (BRDFs), respectively, based on properties derived from the anatomical data. The technique implements both real-time ray tracing and Monte Carlo path tracing, for both volumes and embedded surfaces, to leverage the improved depth and shape perception of natural images in the clinical workflow (e.g., during a surgical procedure).

In a further predecessor system for direct visualization of distances in AR for clinical support, distance data is encoded into parts of the three-dimensional (3D) rendering pipeline, e.g., by tinting the shadows cast by nearby objects or drawing a distance contour during surface shading. A conventional illustrative visualization technique for distance-encoding silhouette edges and surface contours varies line thickness, but the full surfaces are not shown.

In a preferred embodiment, we instead show distances using explicit three-dimensional (3D) glyphs which visually "anchor" the overlay three-dimensional (3D) objects (e.g., the blended overlay image 306) to the real-world organ surfaces (e.g., the background structure 302) in the, e.g., laparoscopy, video feed, as opposed to conventionally modifying the natural appearance of the surfaces or conventionally relying on complicated line patterns.

According to a preferred embodiment, the following acts are performed:

Pre-Operative:

Acquire patient 3D images (in particular including an anatomical structure for generating an overlay image 306) from various modalities.

Perform organ contouring, vessel segmentation, lesion detection, vessel tracing and/or other algorithms related to the image-based surgical guidance.

Perform a deformable registration to reference anatomical models and reference 3D images.

Generate rendering primitives, including but not limited to geometric surfaces, landmarks, lines, and/or glyphs (e.g., for generating the overlay image 306).

Precompute acceleration structures for rendering support (e.g., of a blended version of the overlay image 306), including raytracing acceleration structures (e.g., BVH or K-d trees), signed distance fields (SDF) for real-time distance computations and precomputed lighting information (e.g., irradiance caches).

Continuously During a Surgical Procedure (Also Denoted as Intervention):

Acquire base images or videos (e.g., as background structure 302) for real-time AR guidance, e.g., from a laparoscopic camera.

Detect organs and structures from the images and videos.

a. Perform a real-time deformable registration between organs detected in the live feed, pre-operative segmented organs and reference models and images, using automatically detected landmarks and organ contours.

b. Generate rendering primitives, e.g., organ surfaces to receive rendered shadows.

c. Compute occlusion masks.

Combine the pre-computed SDFs with runtime acquired SDFs of tracked objects, such as tracked surgical devices and/or a surgeon's hands. Acquire head-tracking data for correct perspective of rendered images.

Compute view-dependent rendering primitives, including but not limited to silhouette edges, distance measurement glyphs based on the SDFs, and/or depth enhancement effects such as 3D contour glyphs and surface contours.

Render the Overlay Image or Video:

a. Render a depth image of the scene that includes all primitives to be displayed in AR and has occlusion masks applied.

b. Render the full scene including volume rendering of registered anatomical models and/or pre-operative images (e.g., render the blended overlay image 306 overlayed on the background structure 302 as fused image 314).

i. A preferred embodiment uses photorealistic real-time ray tracing and/or path tracing of geometric and volume data to produce volumetric tinting, ambient occlusions and shadows from the pre-operative images, reference model, and/or live model.

c. Generate the final overlay image (e.g., the fused image 314):

i. Mask structures based on the depth image.

ii. Compute the depth-modulated opacity for blending the overlay (e.g., the overlay image 306) with the acquired real-world images and videos (e.g., including the background structure 302).

Display the augmented visualization via one or more methods, including but not limited to: on a head-mounted display, on tracked monitors and/or display surfaces in the operating room, and/or via projection onto the patient.

The technique, and in particular a preferred embodiment, leverages (e.g., photorealistic) rendering to improve the shape perception and/or depth perception of the user (e.g., the surgeon) by implementing shadowing, ambient occlusions and/or depth of field effects.

Compared to conventional rasterization pipelines, the technique includes ray tracing, which further allows for accurate simulation of the camera lens geometry. The technique can improve the accuracy of the AR rendering since the (e.g., computer-generated) overlay layer (e.g., including a blended version of the overlay image 306) can be matched to the real-world background structure 304 (e.g., camera feed). Implementing such effects in a rasterization pipeline through vertex shaders may require more complex adaptive geometry tessellation. Details can, e.g., be found in the "IEEE Transactions on Visualization and Computer Graphics" contribution by K. Petkov et al. "Interactive Visibility Retargeting in VR Using Conformal Visualization" (Volume 18, Issue 7, July 2012).

Backwards rendering pipelines, e.g., raytracing, may start by generating rays that simulate a camera, including sampling of the lens. Non-liner camera projections (e.g., including a fish-eye lens) that simulate the optics of an endoscopic camera may be easily implemented.

Forward rendering, e.g., rasterization projects, the 3D object onto the viewport and/or implementing complex cameras requires modifying the geometry of the processing pipeline. E.g., on a GPU, such a modification is implemented in a vertex shader state. Alternatively, or in addition, straight geometric edges may be projected to curves under non-linear projections. A complex algorithm may be required to subdivide all mesh edges during rendering, which on a GPU may involve geometry and tessellation shader stages.

Alternatively, or in addition, there exist further rasterization techniques that split the viewpoint into tiles and approximate a non-linear camera with a grid of linear projection cameras.

Alternatively, or in addition, the physically-based light transport simulation allows for accurate matching of the real world (e.g., the background structure 302) and artificial lighting environment, which further improves the illusion that the AR layer (e.g., including a blended version of the overlay image 306) is part of the real-world scene.

Figure 4B:
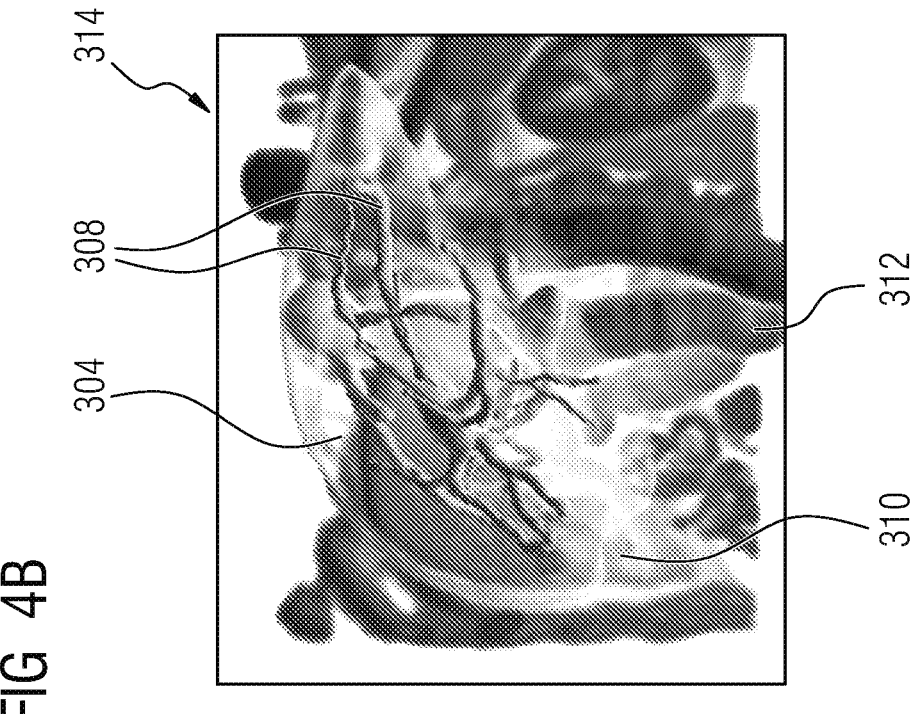
FIGS. 4A and 4B show a comparison of a conventional rasterization overlay and an overlay using a blended overlay image according to an embodiment.
Figure 4A:
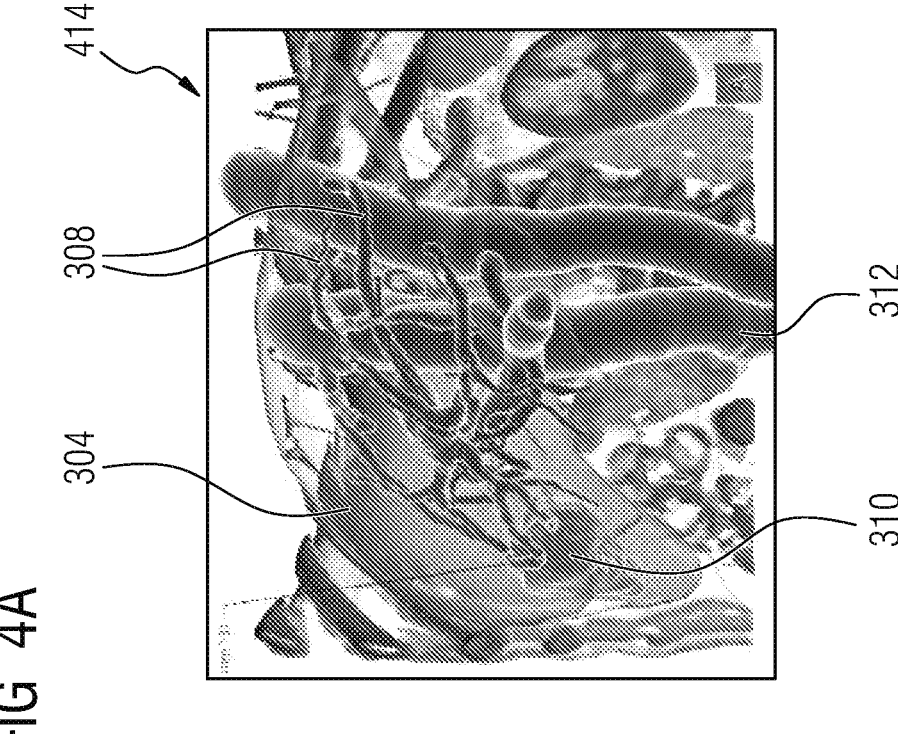

FIGS. 4A and 4B illustrate the difference between rasterization with local illumination shading only (FIG. 4A) and path tracing with global illumination effects according to the invention (FIG. 4B) for the rendering of segmented objects.

The illustrations of FIGS. 4A and 4B may provide examples of rendering (e.g., only and/or without applying the blending of the overlay to a background image). Alternatively, or in addition, both the structures and the (e.g., CT) image may be rendered together in 3D.

The rasterization example 414 of FIG. 4A uses volumetric path tracing for the volume data combined with very fast rasterization of the liver 304, vessels 308; 312 and lesion 310 segmentations, with approximate depth embedding based on depth layers generated by the volume rendering as described in [10].

In FIG. 4A, high quality rendering is combined with very fast mesh rasterization.

In contrast, the path tracing result 314 in FIG. 4B is based on unified rendering of the volume and surface data (e.g., including a blended version of the overlay image 306 and the background structure 302), where the coupled lighting occlusions improve the three-dimensional (3D) spatial understanding.

In some embodiments, the technique may further employ approximate global illumination methods that implement a subset of the visual effects in the path traced image at a fraction of the computational cost. Examples include precomputing a forward-only scattering illumination volume and partially coupling the illumination between the meshes and the volumes (e.g., meshes cast shadows on other meshes but not on the structures from the 3D patient scans). Such an approximation is used for FIGS. 9A and 9B, where the real-time path tracing implementation does not yet provide sufficient image quality on the target graphics processing unit (GPU) hardware at the required framerate.

As part of the rendering pipeline during the surgical procedure (also denoted as interventional procedure), the system continuously outputs images 306 that can be overlaid on top of the laparoscopy video feed 302, or other base images, on the AR display.

Figure 5A:
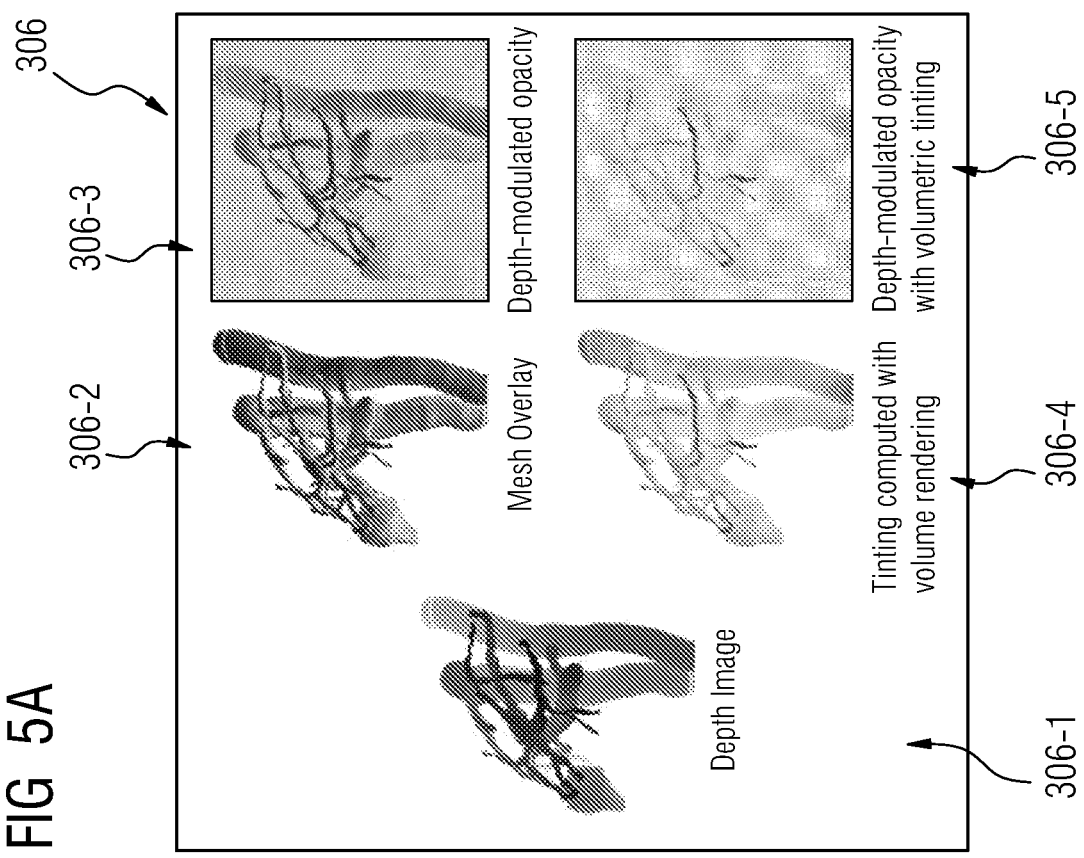
FIGS. 5A and 5B show different versions of an example overlay image with and without depth-modulated opacity and with and without volumetric color tinting as well as the corresponding overlayed images on the background structure.
Figure 5B:
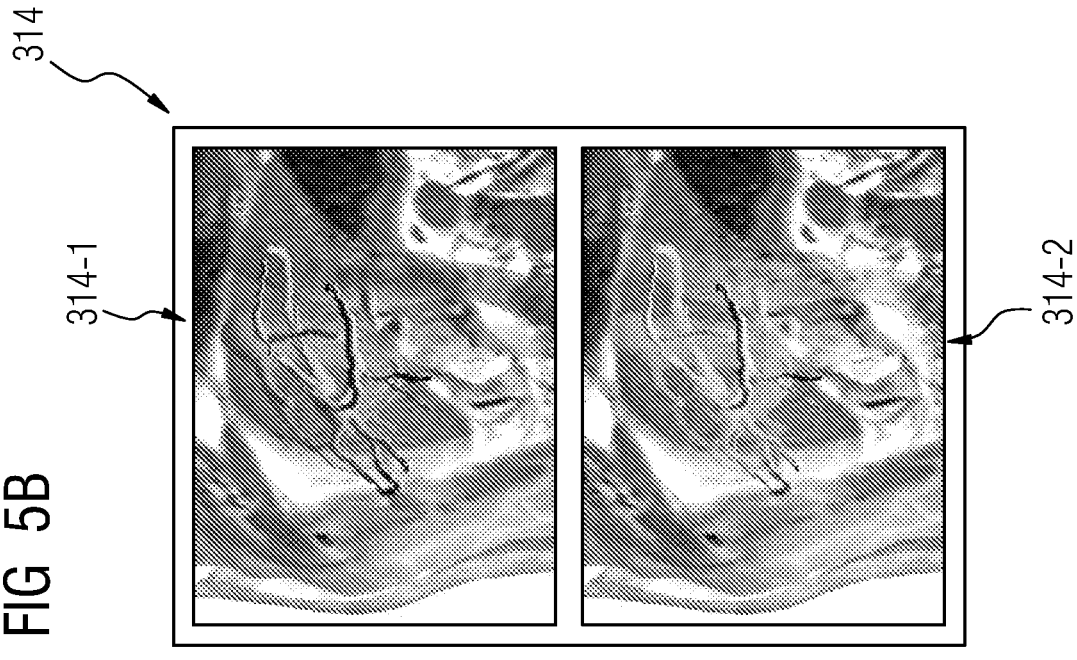

FIGS. 5A and 5B show an example depth image 306-1 generated by the rendering of the vessel and lesion segmentation data. The opacity of a base mesh overlay 306-2 of the depth image 306-1 is modulated based on a depth image, e.g., leading to the depth modulated opacity image 306-3. Overlay data, e.g., the depth image 306-1, is embedded in a registered pre-operative or reference dataset for accurate tinting computation by volume rendering, e.g., leading to the tinted image 306-4. By combining depth modulated opacity, e.g., according to the depth-modulated opacity image 306-3, with tinting (also: color tinting, or volumetric coloring), a further version 306-5 of the overlay image 306 may be produced.

Any one of the overlay examples 306-1; 306-2; 306-3; 306-4; 306-5 may use the rendering technique described in the context of FIG. 4B. Alternatively, or in addition, the 3D structures may be rendered (e.g., separately). By this, an AR use case may be approximated and/or accomplished.

In the example of FIGS. 5A and 5B, depth values in camera space are used to modulate the opacity of the overlay, so that during final compositing, structures farther from the user fade away (as depicted, e.g., in the images 306-3 and 306-5) and provide the surgeon (also: user) with an important visual cue for understanding the complex spatial structures of the vessel tree and its relationship to both the, e.g., liver, background anatomy and the detected lesion.

The (volumetric and/or color) tinting of the mesh overlay image 306-4 is achieved by embedding the three-dimensional (3D) geometries in the volumetric anatomy of the patient and performing volume rendering with a preset which closely mimics the visual appearance of the organ in the real-world for the given imaging modality (e.g., CT images in FIGS. 5A and 5B). Other embodiments may use a reference anatomical three-dimensional (3D) image registered to the detected surfaces in the video feed (e.g., including the background structure 302), or other registered models, such as mesh models for the anatomical context (and/or background structure 302). The renderer may also use additional sources of occlusion at this stage, such as occlusion masks from the surgeons (also: user's) hands segmented from the video feed, or other detected organs (e.g., as the background structure 302). The renderer may simulate full or partial optical occlusion, or apply non-physical effects (e.g., render silhouette edges only for occluded surfaces, such as surfaces included in the overlay image 306). In other embodiments, the color tinting may use a simplified model with homogeneous participating media instead of registered anatomical three-dimensional (3D) images (e.g., as the anatomical structure of the overlay image 306).

The image 314-1 in FIG. 5B shows as first example, in which the background structure 302 is overlayed with the depth-modulated opacity image 306-3. The image 314-2 in FIG. 5B shows a second example, in which the background structure 302 is overlayed with the depth-modulated opacity with volumetric tinting image 306-5.

Figures 6A, 6B, 6C, 6D:
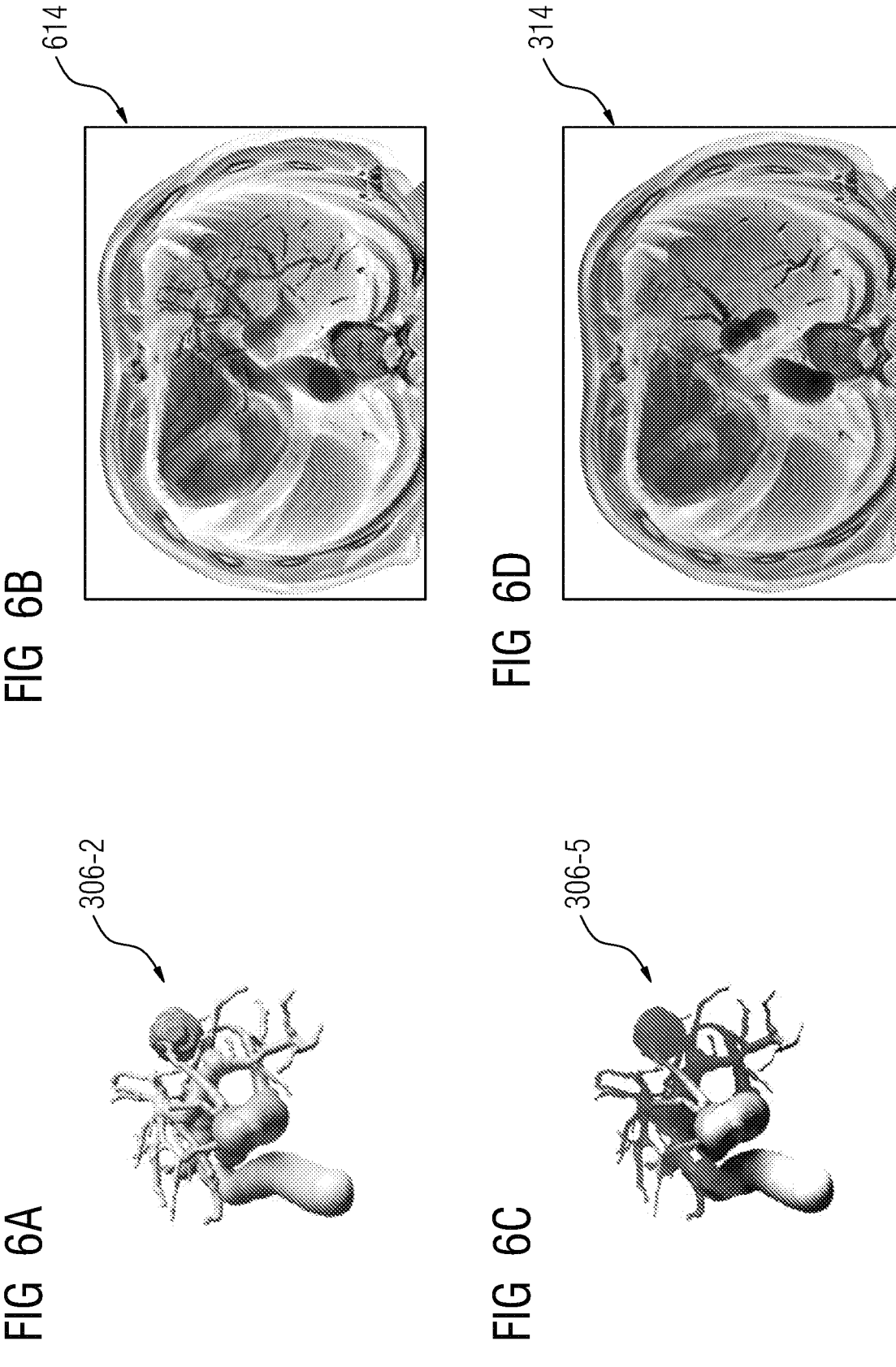
FIGS. 6A, 6B, 6C and 6D show a comparison of a conventional fixed opacity overlay image and the blended overlay image according to an embodiment as well as the corresponding overlayed images onto the background structure.

FIGS. 6A, 6B, 6C and 6D show an exemplary comparison between methods for generating a simple overlay (FIGS. 6A and 6B) with including visual depth cues that allow for faster understanding of three-dimensional (3D) spatial relationships (FIGS. 6C and 6D) compared to the simple overlay (FIGS. 6A and 6B).

In the example of FIGS. 6A to 6D, a different anatomical orientation is shown compared to the preceding examples of FIGS. 3A to 5B. FIG. 6A shows the mesh layer 306-2 using a fixed opacity, which results in limited visual cues for resolving depth in the overlayed image 614 shown in FIG. 6B. This may be contrasted with an overlay using both depth-modulated opacity and the model-based volumetric coloring, as exemplified in the overlay image 306-5 in FIG. 6C and the resulting overlayed image 314 in FIG. 6D.

The technique introduces the direct visualization of distances on the AR overlay. The 3D visualization is specifically "anchored" to detected surfaces in the, e.g., laparoscopy, video feed, and/or in other real-world imagery, so that a surgeon (also: human observer) can more easily perceive the spatial relationships with the computer-generated graphics.

Figure 7:
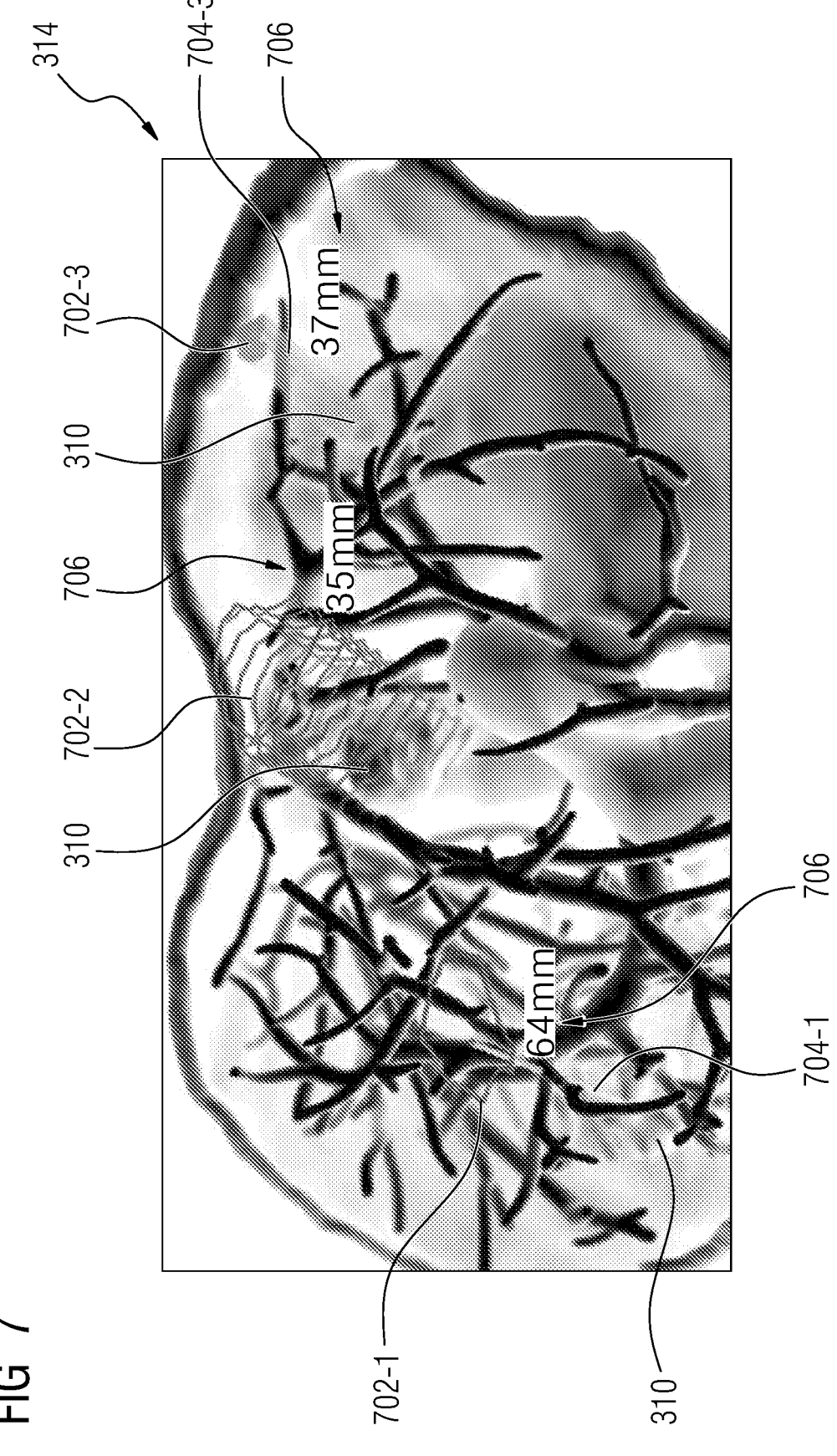
FIG. 7 shows an example of using glyphs for conveying distance information precisely and explicitly regarding lesions or other regions of interest (ROIs)

FIG. 7 illustrates connecting visualization techniques, where the top surface of an organ, e.g., the liver, will be provided by the real-world image (e.g., as the background structure 302) during surgery. From left to right for each lesion, FIG. 7 shows:

a. The silhouette 702-1 of a lesion and/or tumor onto the detected liver surface from the laparoscopy video is provided along with the direction to the closest point. The distance to the lesion is visualized directly by a connecting line 704.1. The distance may optionally further be visualized by a numerical depth indication 706.

b. The projection of the lesion onto the closest point of the detected liver surface is shown as a single contour 702-2, as in 1. Further flat contours 702-2 are shown in three-dimensional (3D) space at regular (e.g., 5 millimeter, 5 mm) intervals for a stronger visual connection to the lesion 310. The distance to the lesion, e.g., from the foremost (also: the most protruding) contour 702-2, may also be explicitly visualized by the numerical depth indication 706.

c. The silhouette 702-3 of the lesion 310 is extruded along the direction to the nearest point on the detected liver surface. This visualization uses a fixed semi-transparent material, but further embodiments may use material variations along the generated 3D structure. The distance to the lesion may also be explicitly provided by the numerical depth indication 706.

The distance visualizations 702-1, 702-2, 702-3, 704-1, 704-3, from the lesions 310 to the closest points on the occluding surface, as used for overlay generation, in FIG. 7 may also be denoted as: (1) distance line and lesion outline projection; (2) lesion outline projection rings at regular (e.g., 5 mm) intervals; and (3) extruded lesion silhouette.

In all three cases, the method (and/or the system) may apply the same techniques as the rest of the visualization, including the distance-modulated opacity (e.g., analogous to the image 306-3) and the volumetric tinting (e.g., analogous to the image 306-4 or 306-5). A direct text display 706 of the detected distance value may optionally be included in any of the three cases. Alternatively, or in addition, implementations may mix the features, or subsets of the features, from the three cases (also denoted as demonstrations).

Figures 8A, 8B, 8C:
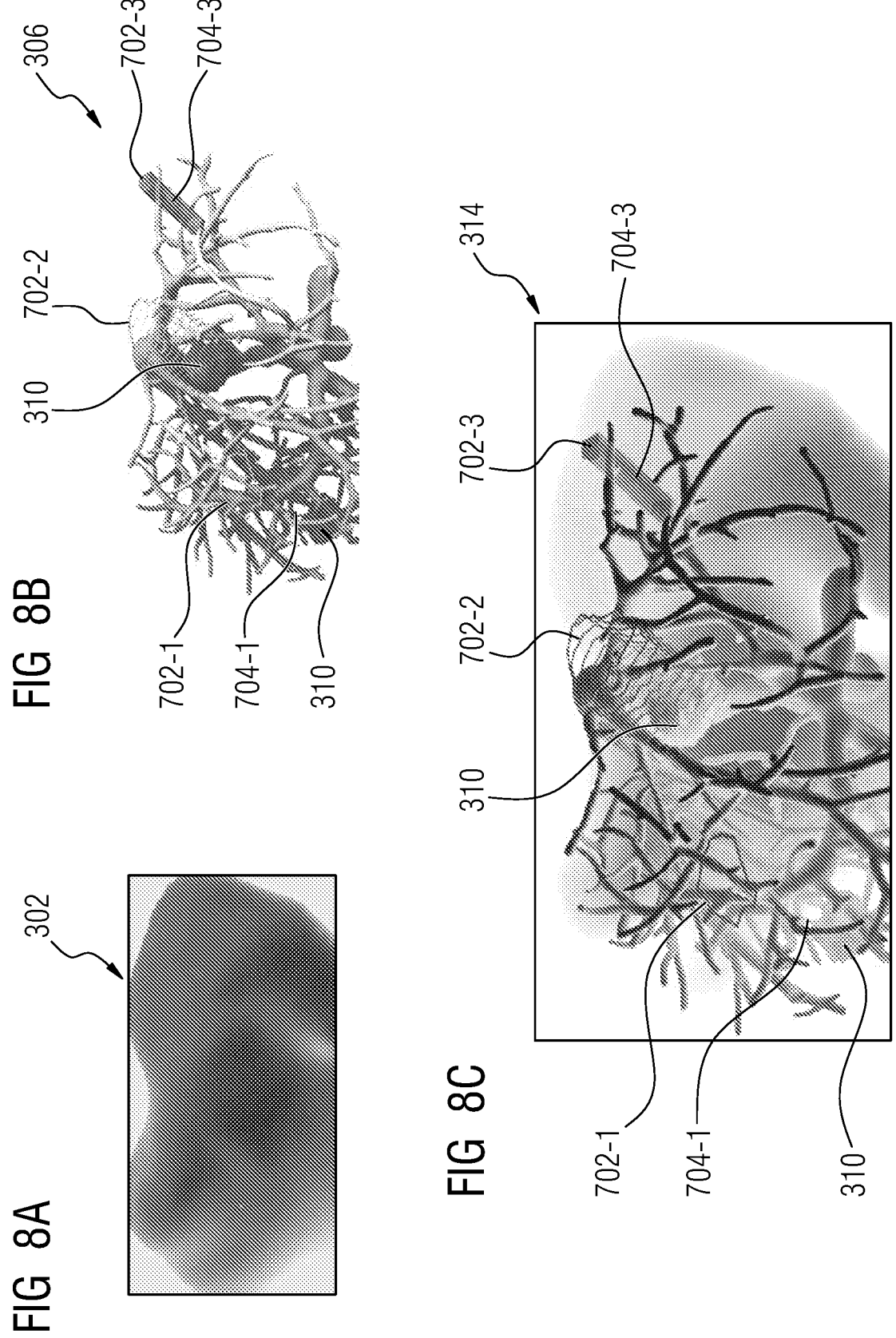
FIGS. 8A, 8B and 8C show details of generating the overlayed image including glyphs according to the embodiment of FIG. 7.

Glyphs for distances between detected organs or regions of interest (ROIs) and other tracked objects, such as surgical devices, may be generated at runtime (also: in real-time) based on the pre-computed SDFs and/or other data. FIGS. 8A, 8B and 8C further show an example where the visualization in FIG. 7 is used as an overlay in an AR application.

FIG. 8A shows the background structure 302. FIG. 8B shows the overlay image 306. FIG. 8C shows the overlayed image 314 (also: the compositing with overlay data, or the fused image) generated for the visualization in FIG. 7. The overlay rendering of the example in FIGS. 8B and 8C uses opacity modulation and volumetric tinting.

For clarity, in FIGS. 8A, 8B and 8C everything other than the distance glyphs 702-1, 702-2 and 702-3 and the lesions 310 is shown in a neutral color, but in a practical implementation, the base image 302 may use (e.g., colorful) frames from the real-world camera.

Figure 9A:
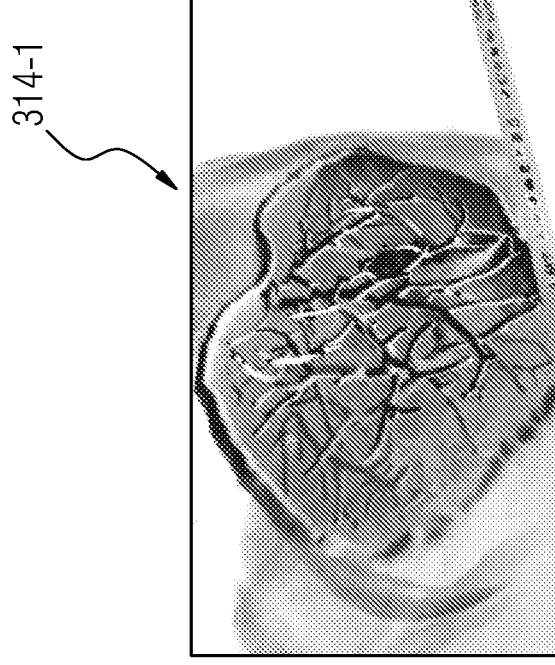
FIGS. 9A and 9B show two examples of approximations of rendering an overlayed image including the blended overlay image and the background structure using a stereoscopic display and a virtual reality headset, respectively.
Figure 9B:
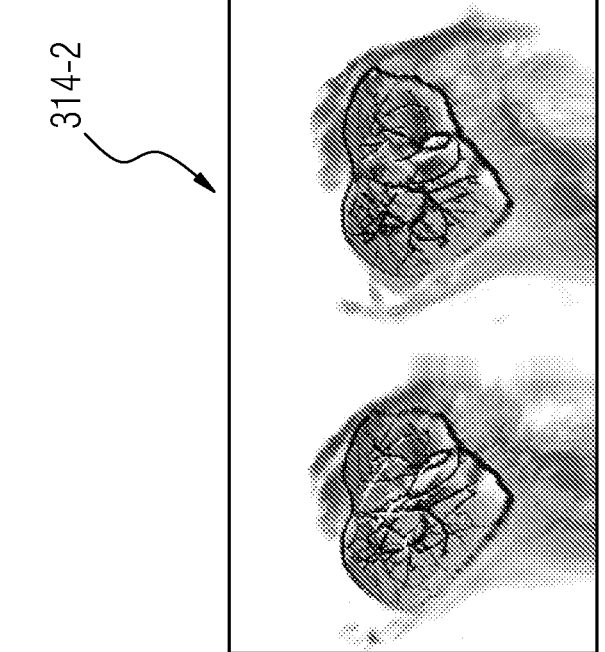

In practical applications, motion parallax can enhance the spatial understanding of the three-dimensional (3D) scene, even in the absence of the visual effects discussed so far. The effect of applying the method is even more pronounced when coupled with stereoscopic rendering and/or when generating the overlayed image 314 on immersive displays. FIGS. 9A and 9B show early examples of the visualization system running on a stereoscopic display (FIG. 9A) and on a virtual reality headset (FIG. 9B), both with head tracking. Both deployments in FIGS. 9A and 9B further use simplified ray tracing for the segmentation data and interactive volumetric lighting for the anatomy rendering 314-1; 314-2 due to the real-time performance requirements of the target display systems. A limited version of head-tracking of FIG. 9A can be implemented, e.g., for large monoscopic displays in the operating room (also: operating theater). Another preferred deployment uses stereoscopic head-tracked AR headsets according to FIG. 9B.

In the example of FIG. 9A, (e.g., real-time and/or actual) CT data are used for the background structure 302 (e.g., instead of a static volumetric fog).

The approximation technique in FIG. 9A implements a fast anatomy rendering for the anatomy with a subset of the global illumination effects (e.g., still considered as photorealistic lighting). The overlay rendering uses raytracing for the meshes.

The renderings of FIGS. 9A and 9B may be improved analogously to the techniques described in the context of FIG. 6D.

Wherever not already described explicitly, individual embodiments, or their individual aspects and features, described in relation to the drawings can be combined or exchanged with one another without limiting or widening the scope of the described invention, whenever such a combination or exchange is meaningful and in the sense of this invention. Advantages which are described with respect to a particular embodiment of the present invention or with respect to a particular figure are, wherever applicable, also advantages of other embodiments of the present invention.

The invention claimed is:

1. A computer-implemented method for providing an overlayed image, comprising the method steps of:
   receiving data indicative of an anatomical structure;

generating an overlay image of the anatomical structure from the received data;
   determining a background structure serving as a background for the overlay image of the anatomical structure;
   blending the overlay image of the anatomical structure by a depth enhancement model relative to the background structure to generate a blended overlay image, wherein the blending comprises a color tinting of the overlay image and not the background structure, wherein the color tinting comprises a coloring relative to a predetermined value depending on the background structure; and
   overlaying the blended overlay image of the anatomical structure on the background structure.

2. The computer implemented method according to claim 1, wherein the blending comprises blending with a depth modulated opacity.

3. The computer implemented method according to claim 1, wherein the overlay image is configured to provide optical guidance in a surgical procedure, and the received data is indicative of the anatomical structure relative to a surgical procedure.

4. The computer implemented method according to claim 3, wherein the background structure is selected from a group consisting of: image data acquired in a pre-operative scan, and live image data acquired during the surgical procedure.

5. The computer implemented method according to claim 3, wherein the surgical procedure comprises an open surgery, and wherein the background structure comprises a part of a body on which the surgical procedure is performed.

6. The computer implemented method according to claim 1, wherein the blending comprises a fading of the overlay according to a depth relative to the background structure, wherein a degree of fading corresponds to the depth within the background structure.

7. The computer implemented method according to claim 1, wherein a depth perception is obtained by a signed distance field, SDF, Monte Carlo path tracing, and/or a ray tracing acceleration structure.

8. The computer implemented method according to claim 7, wherein a data structure for the depth perception comprises a bounding volume hierarchy, BVH, and/or a K-dimensional tree.

9. The computer implemented method according to claim 1, wherein overlaying the blended overlay image comprises rendering the blended overlay image using a video stream on a display.

10. The computer implemented method according to claim 1, wherein generating the overlay image of the anatomical structure comprises generating the overlay image by primitives.

11. The computer implemented method according to claim 1, wherein the blending further comprises generating a glyph indicative of an extent and/or a depth of at least part of the anatomical structure, wherein the glyph comprises at least one of:
   a number of superimposed contours;
   a distance line and/or an extruded contour, wherein a tip of the distance line and/or of the extruded contour denotes a position of the at least part of the anatomical structure; or
   a numerical depth indication.

12. The computer implemented method according to claim 11, wherein the glyph comprises the number of superposed contours, and wherein an intensity of the blending is varied so that at least one of the intensity, a line thickness, and/or a length and/or a distance of dashes or dots, of the contour is increased for the contour nearest to an observer and the intensity, the line thickness, and/or the length and/or the distance of dashes or dots, of the contour is diminished for the contour farthest from the observer.

13. The computer implemented method according to claim 1, wherein the overlaying comprises prioritizing a surgical device over the blended overlay image, wherein prioritizing the surgical device comprises the surgical device occluding the anatomical structure when the depth of the anatomical structure lies below the surgical device.

14. A system for providing optical guidance, the system comprising:

an interface configured to receive data indicative of an anatomical structure; and a renderer configured to:

generate an overlay image of the anatomical structure from the received data;

determine a background structure serving as a background for the generated overlay image of the anatomical structure;

blend the generated overlay image of the anatomical structure by a depth enhancement model relative to the background structure to generate a blended image, wherein the renderer is configured to blend by a color tinting of the overlay image and not the background structure, wherein the color tinting comprises a coloring relative to a predetermined value depending on the background structure; and overlay the blended image of the anatomical structure on the background structure.

15. The system of claim 14 wherein the renderer is further configured to blend as a fade of the generated overlay according to a depth relative to the background structure, wherein a degree of fading corresponds to the depth within the background structure.

16. A non-transitory computer-readable medium on which instructions are stored that can be read and executed by a server to provide optical guidance, the instructions comprising:

generation of an overlay image of the anatomical structure from the received data;

determination of a background structure serving as a background for the generated overlay image of the anatomical structure;

blend the generated overlay image of the anatomical structure by a depth enhancement model relative to the background structure to generate a blended image, wherein the renderer is configured to blend by a color tinting of the overlay image and not the background structure, wherein the color tinting comprises a coloring relative to a predetermined value depending on the background structure; and overlay of the blended image of the anatomical structure on the background structure.

* * * * *